United States Patent [19]
Discko, Jr.

[11] Patent Number: 5,324,273
[45] Date of Patent: Jun. 28, 1994

[54] DISPOSABLE BARREL DENTAL IMPRESSION MATERIAL SYRINGE

[75] Inventor: John J. Discko, Jr., Hamden, Conn.

[73] Assignee: Centrix, Inc., Shelton, Conn.

[21] Appl. No.: 954,580

[22] Filed: Sep. 30, 1992

[51] Int. Cl.⁵ ............................................. A61M 5/00
[52] U.S. Cl. ................................. 604/240; 604/218; 604/311; 433/90
[58] Field of Search ............... 604/51, 59, 60, 185, 604/218, 226, 231, 240, 241, 239, 82, 93, 90, 89; 433/80, 82, 83, 85, 87, 89, 90

[56] References Cited

U.S. PATENT DOCUMENTS

| | | |
|---|---|---|
| 1,139,975 | 5/1915 | Hopper. |
| 2,034,294 | 3/1936 | Hein. |
| 3,290,946 | 12/1966 | Pursell. |
| 3,364,002 | 1/1968 | Michel. |
| 3,900,954 | 8/1975 | Dragan .................. 433/90 |
| 4,002,174 | 1/1977 | Reed et al.. |
| 4,492,576 | 1/1985 | Dragan .................. 433/90 |
| 4,540,405 | 9/1985 | Miller et al.. |
| 4,784,607 | 11/1988 | Francois .................. 433/90 |

FOREIGN PATENT DOCUMENTS 0795630  5/1958  United Kingdom ............... 604/241

Primary Examiner—C. Fred Rosenbaum
Assistant Examiner—Vanitha Alexander
Attorney, Agent, or Firm—Paul A. Fattibene; Arthur T. Fattibene

[57] ABSTRACT

A disposable barrel dental impression syringe having a rotatable malleable needle cannula. A disposable barrel is fitted with a malleable needle cannula that is seated to permit easy rotation thereof. A handle is threaded onto the open end of the barrel. A plunger is fitted through the handle and barrel forming a syringe for the extrusion of dental impression material. The needle cannula is positioned within the discharge end of the barrel in such a way to permit easy rotation, yet prevent pushing or pulling the needle cannula through the discharge end of the barrel. This permits exact positioning of the needle cannula for placement of dental impression material. Additionally, only the barrel portion of the syringe being disposable, the precision and feel of a high quality impression syringe is maintained.

6 Claims, 2 Drawing Sheets

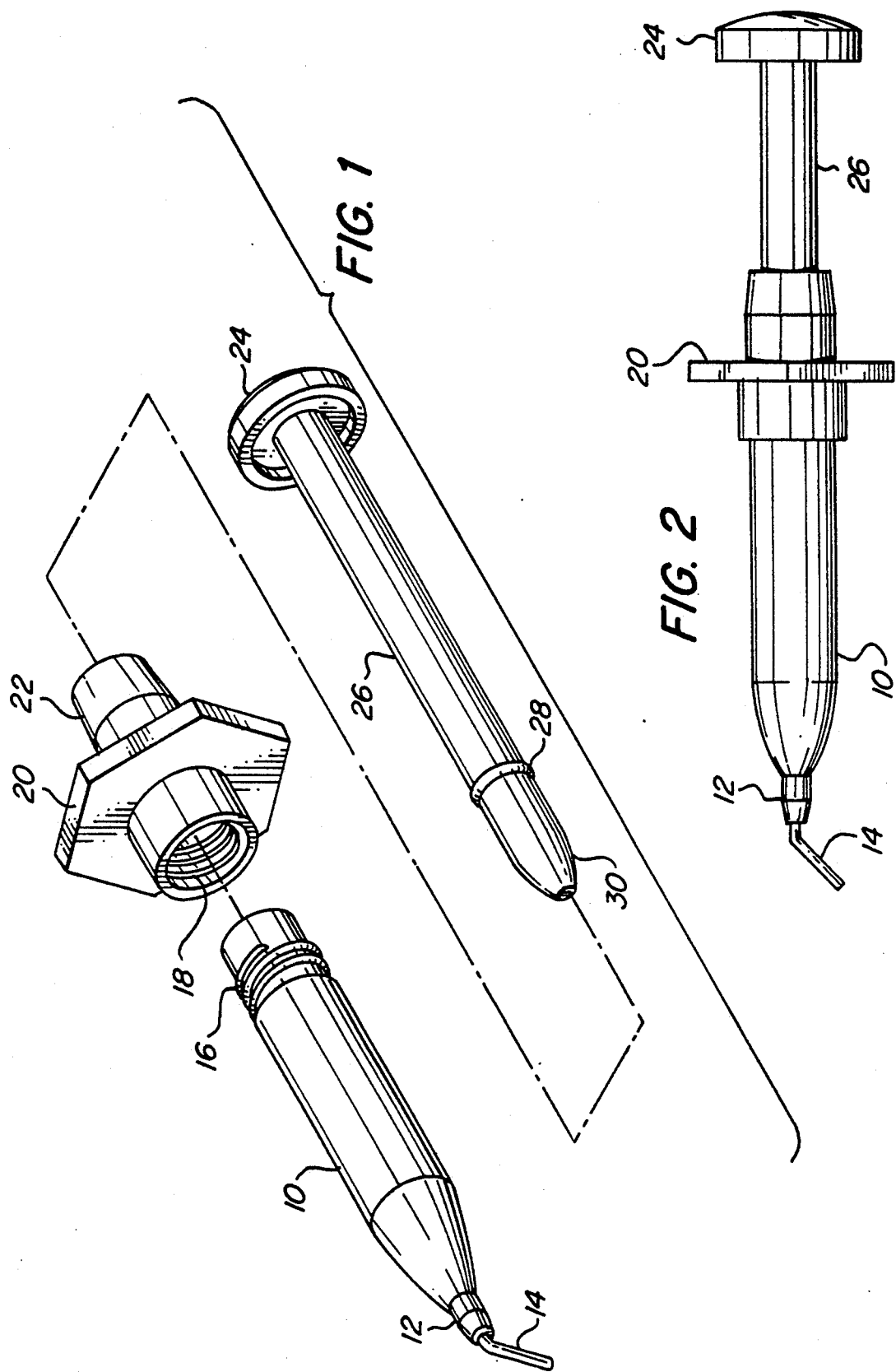

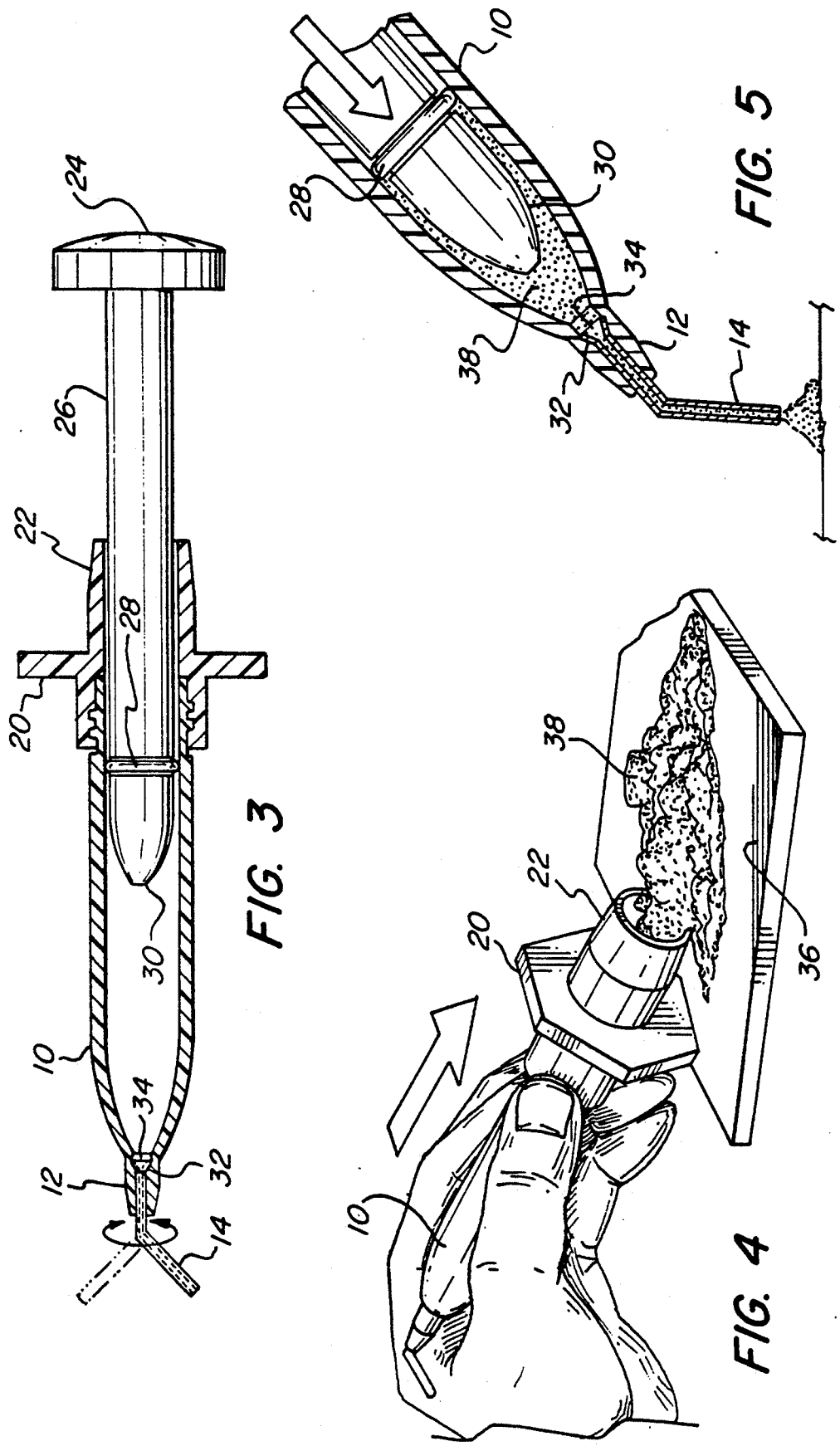

DISPOSABLE BARREL DENTAL IMPRESSION MATERIAL SYRINGE

FIELD OF THE INVENTION

The present invention relates generally to a delivery system for placement of dental impression material, and more particularly to a disposable barrel having a rotatable malleable cannula therein.

BACKGROUND OF THE INVENTION

Dental impression material is used in many dental procedures in order to obtain an accurate impression of the mouth and teeth of a patient. Typically, the impression material used is initially able to be syringed for placement around the teeth and mouth, and then cures into a rubber-like material. An accurate impression of the teeth and gums is thereby obtained and used for the manufacture of customized dental devices. Typically, the dental impression material is syringed through a standard bulk syringe having a stainless steel barrel and hub attached thereto. Within the hub is placed a disposable tip. Most of the impression material is contained within the stainless steel barrel and only a small portion of the impression material is contained within the disposable tip. While this delivery system accomplished the goal of the placement of impression material, these devices have not lent themselves to convenient and efficient use by the dentist. These impression syringes have to be disassembled and scrubbed carefully in order to remove all of the cured impression material. This is a time consuming and tedious process. Additionally, a portion of the syringe barrel necessarily entering the patient's mouth would have to be disinfected in order to prevent cross-contamination between patients.

Therefore, there is a need for an improved dental impression syringe that is easy and convenient to use for the dentist that will eliminate the potential for cross-contamination.

SUMMARY OF THE INVENTION

The present invention is directed to a delivery system for the dispensing of dental impression material. A disposable barrel is used in conjunction with a handle and plunger to form a syringe. The barrel is formed to contain a reservoir of dental impression material and is intended to be discarded after use. The barrel has placed therein a needle cannula which is bendable and easily rotated. The cannula has a flared portion which is seated into the discharge end of the barrel. A plunger is used having the advancing end complimentary shaped with that of the interior dimension of the barrel so that substantially all of the impression material therein is extruded. The handle has an open end that is externally tapered facilitating the placement of impression material therein.

It is an object of the present invention to provide a syringe for the dispensing and placement of dental impression material that is convenient and easy for the dentist to use.

It is an object of the present invention to provide the dentist with a syringe that combines the precision and feel of a high quality impression syringe with the convenience of disposability.

It is an advantage of the present invention that the needle cannula is bendable and rotatable facilitating placement of the impression material.

It is a feature of the present invention that the barrel portion of the syringe is disposable.

It is another feature of the present invention that the rear portion of the handle is externally tapered for easy loading of the dental impression material.

BRIEF DESCRIPTION OF THE DRAWINGS

FIG. 1 is an exploded perspective view of the present invention.

FIG. 2 is a side elevational view of the present invention.

FIG. 3 is a partial longitudinal cross-section of the invention.

FIG. 4 is a perspective view illustrating loading of the present invention.

FIG. 5 is a partial longitudinal cross-section of a portion of the invention.

DETAILED DESCRIPTION OF THE PREFERRED EMBODIMENT

FIG. 1 illustrates the present invention. A disposable barrel 10 made of a plastic material has a discharge tip 12 at one end. The discharge tip 12 is formed as a part of or integrally with the barrel. Within discharge tip 12 is a needle cannula 14. The needle cannula 14 is malleable and rotatable within the discharge tip 12. The other end of disposable barrel 10 is open and has male threads 16. Handle 20 has female threads 18 thereon. The handle 20 threads onto disposable barrel 10. The rear end of handle 20 has a tapered portion 22. Between the tapered portion 22 and the female threads 18, the handle 20 has a hexagonal shaped finger plate placed perpendicular to the longitudinal axis of the primarily cylindrical handle 20. This hexagonal shaped finger plate prevents rolling of the syringe when placed on a flat surface. Fitting through handle 20 and disposable barrel 10 is a plunger. The plunger is comprised of a plunger cap 24, a shaft 26, an O-ring seal 28, and a plunger end 30. The plunger end 30 is shaped to compliment the interior front surface of barrel 10.

FIG. 2 illustrates the present invention in an assembled form.

FIG. 3 is a partial cross-section of the present invention. FIG. 3 more clearly illustrates the construction of the discharge tip 12. The discharge tip 12 has a relatively long solid portion with a bore therethrough. Through this bore is placed the needle cannula 14. The needle cannula 14 comprises a metal needle having a gauge size that can range between 14 and 30. Needle cannula 14 has a flare or flange 34 at the rear thereof. The flange 34 is of the shape of a funnel having sides that are oblique to the longitudinal axis of the needle cannula 14. The flange 34 is secured in a seat 32 formed in the interior surface of the discharge tip 12. The flange 34 and seat 32 prevent the needle cannula 14 from being pulled or pushed out of the discharge tip 12. However, the needle cannula 14, not being cemented or molded into the discharge tip 12, can be rotated 360 degrees. The flange 34 additionally seals the discharge tip 12 preventing impression material from leaking out around the outside diameter of the needle cannula 14. The discharge tip 12 has a bore therethrough which permits a friction fit with the outside diameter of needle cannula 14. The length of the discharge tip 12 and bore therein is sufficiently long to provide support for the needle cannula 14. Therefore needle canula 14 can be bent without dislodging or loosening the needle cannula 14 therein. The disposable barrel 10 is preferably made of an inexpensive plastic that is relatively soft so that the flange 24 at the rear of the needle cannula 14 is set or seats into the seat 32. The outer edges of the flange 34 tend to dig into the relatively soft plastic material preventing rearward movement once set, while still permitting rotation. Additionally, this reduces the cost and complexity of manufacturing compared to molding or gluing the needle cannula 14 into place. This, in combination with the malleability of the needle cannula 14, permits the needle cannula 14 to be positioned for easy access in the oral cavity by the dentist. The present invention is related to U.S. Pat. No. 5,052,927 entitled "Syringe and Disposable Capsule With Cannula For Use Therein" issuing to John Discko, Jr., the same inventor as in the present application, on Oct. 1, 1991, and is herein incorporated by reference.

FIG. 4 illustrates one method of filling the present invention with dental impression material. Typically, dental impression material is comprised of two components. These two components must be mixed permitting chemical interaction to cure the impression material. After mixing, the dental impression material 38 on a mixing palette 36, the dental material 38 is placed within the syringe of the present invention. With the handle 20 threaded onto the disposable barrel 10, the dental material 38 is scraped into the handle 20 and barrel 10. The taper 22 formed on the rear portion of the handle 20 assists in the scraping of dental impression material 38 into the handle 20 and barrel 10 assembly. This can quickly be done with a back and forth motion. Once a sufficient amount of dental impression material 38 is placed within the handle 20 and barrel assembly, the plunger assembly is inserted through the rear portion of the handle 20. The dental impression material can then be extruded as needed by the dentist.

FIG. 5 more clearly illustrates the operation of the present invention in syringing or extruding dental impression material 38. As should be appreciated, after the dental impression material 38 sets, a rubber-like substance is formed which prohibits easy cleaning of the barrel 10 and needle cannula 14 assembly. Therefore, the barrel 10 and needle cannula 14 assembly are discarded after use. The plunger assembly and the handle 20 being of relatively good quality parts are cleaned and retained for use with another barrel 10 and needle cannula 14 assembly. Therefore, the precision and feel of a quality syringe is maintained with the convenience of avoiding difficult cleaning of the cured impression material. Additionally, cross-contamination is avoided. The rotatability and malleability of the needle cannula 14 facilitate easy placement of the impression dental material by the dentist.

Therefore, it should be readily appreciated that the present invention provides an easy and convenient solution to the difficult task of working with dental impression material.

What is claimed:

1. A disposable barrel dental impression material syringe comprising:
   a plastic disposable barrel having a first longitudinal bore, said barrel having an open end and a discharge end having an integral discharge tip with a second longitudinal bore therein coaxial with the first longitudinal bore;
   a malleable metal needle cannula having a substantially constant outside diameter inserted through the second longitudinal bore of said discharge tip, said cannula having a flared flange at one end whereby said cannula is retained within the second longitudinal bore of said discharge tip;
   a handle;
   means, associated with said handle and said barrel, for attaching said open end of said barrel to said handle;
   a plunger, said plunger slidably fitting within the first longitudinal bore of said barrel in the open end, whereby dental impression material is extruded through said cannula when said plunger is advanced in the first longitudinal bore in said barrel.

2. A disposable barrel dental impression material syringe as in claim 1 further comprising:
   an externally tapered portion on the rear end of said handle.

3. A disposable barrel dental impression material syringe as in claim 1 wherein:
   said means for attaching said handle and the open end of said barrel together comprise a male and female thread.

4. A disposable barrel dental impression material syringe as in claim 1 wherein:
   said plunger has a shape complimentary to the internal shape of said barrel.

5. A disposable barrel dental impression material syringe comprising:
   a plastic disposable barrel, said barrel having an open end and a discharge end having an integral discharge tip, said discharge tip having a bore therethrough;
   a malleable metal cannula having a substantially constant outer diameter extending through said discharge tip, said cannula being projected through the bore of the discharge tip to extend beyond the end of the discharge tip, and said cannula having means formed at an end thereof with said means being of one piece with said cannula for positively retaining, sealing and rotatively connecting said cannula relative to said discharge tip for 360 degree rotation relative to said discharge tip;
   a cylindrical handle attaching to said plastic disposable barrel; and
   a plunger, said plunger slidably fitting within said barrel,
   whereby dental impression material is extruded through said cannula when said plunger is advanced in said barrel.

6. A disposable barrel dental impression material syringe comprising:
   a plastic disposable barrel, said barrel having an open end and a discharge end, the open end having external male threads formed thereon;
   an integrally formed discharge tip formed within the discharge end of said barrel, said discharge tip having a bore therethrough;
   a funnel shaped seat formed on one end of said discharge tip adjacent the interior of said barrel;
   a malleable metal needle cannula having a substantially constant outside diameter and having a gauge size between 14 and 30 inserted through the bore and having an outer diameter to form a friction fit with the bore;
   a funnel shaped flared flange formed on one end of said needle cannula and shaped to fit within said funnel shaped seat whereby said cannula is retained within said discharge tip, yet permitted to rotate;
   a cylindrical handle, said handle having internal female threads formed in one end, and an externally tapered diameter at the other end, said handle having a hexagonal finger plate placed perpendicularly with respect to the longitudinal axis of said cylindrical handle between the internal female treads and the externally tapered diameter; and a plunger, said plunger slidably fitting within said barrel, and having a front end shaped to complement the discharge end of said barrel, whereby substantially all dental impression material is extruded through said needle cannula when said plunger is advanced in said barrel.

* * * * *